US010426346B2

(12) United States Patent
Lee et al.

(10) Patent No.: US 10,426,346 B2
(45) Date of Patent: Oct. 1, 2019

(54) OPTICAL TOMOGRAPHY DIGITAL IMPRESSION IMAGING SYSTEM AND METHOD FOR USE THEREOF

(71) Applicant: National Yang Ming University, Taipei (TW)

(72) Inventors: Shyh-Yuan Lee, Taipei (TW); Chih-Wei Lu, New Taipei (TW); Dong-Yuan Lyu, New Taipei (TW); Yu-Chen Lai, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 15/778,889

(22) PCT Filed: Nov. 26, 2015

(86) PCT No.: PCT/CN2015/095629
§ 371 (c)(1),
(2) Date: May 24, 2018

(87) PCT Pub. No.: WO2017/088139
PCT Pub. Date: Jun. 1, 2017

(65) Prior Publication Data
US 2018/0353078 A1    Dec. 13, 2018

(51) Int. Cl.
*A61B 5/00* (2006.01)
*A61C 9/00* (2006.01)

(52) U.S. Cl.
CPC .......... *A61B 5/0066* (2013.01); *A61B 5/0073* (2013.01); *A61B 5/0088* (2013.01); *A61C 9/0053* (2013.01); *A61B 2576/02* (2013.01)

(58) Field of Classification Search
CPC .............. A61C 9/0053; G01B 9/02091; A61B 5/0066; A61B 5/0088
See application file for complete search history.

(56) References Cited

U.S. PATENT DOCUMENTS

| 2002/0006217 A1 * | 1/2002 | Rubbert | .................. A61C 7/00 |
| | | | 382/131 |
| 2005/0024646 A1 * | 2/2005 | Quadling | ............. A61B 5/0066 |
| | | | 356/477 |
| 2009/0227875 A1 | 9/2009 | Cao et al. | |

(Continued)

FOREIGN PATENT DOCUMENTS

| CN | 101563021 A | 10/2009 |
| CN | 104000557 A | 8/2014 |
| WO | WO 2004/100068 A2 | 11/2004 |

*Primary Examiner* — Jonathan M Hansen
(74) *Attorney, Agent, or Firm* — Muncy, Geissler, Olds & Lowe, P.C.

(57) ABSTRACT

Provided are an optical tomography digital-impression imaging system and a method for use thereof, said system including: an optical coherence tomography scanner, used for obtaining tomographic slice thicknesses of a plurality of tissue areas of each optical tomography digital image; an information analysis and processing component electrically connected to the optical coherence tomography scanner. The information analysis and processing component has a refractive index compensation and optical path correction functions; by way of analysis and processing, tomographic slice thickness correction values corresponding to the tissue areas are obtained, thus establishing a digital model of the tissue areas.

12 Claims, 9 Drawing Sheets

(56) References Cited

U.S. PATENT DOCUMENTS

2012/0322025 A1* 12/2012 Ozawa ................ A61C 9/0053
433/29
2018/0027159 A1* 1/2018 Dillon ................ A61B 5/0066
348/66

* cited by examiner

OPTICAL TOMOGRAPHY DIGITAL IMPRESSION IMAGING SYSTEM AND METHOD FOR USE THEREOF

RELATED APPLICATIONS

This is a National Phase application filed under 35 U.S.C. 371 as a national stage of PCT/CN2015/095629 filed Nov. 26, 2015, the content of which is hereby incorporated by reference in its entirety.

FIELD OF THE INVENTION

The present invention relates to an optical tomography digital impression imaging system and method for use thereof. It uses Optical Coherence Tomography (OCT) technique to image the tooth structure to obtain the structural information of tooth surface and the tooth-gum boundary under the gum. The refractive index of tissue is compensated to obtain the positions of teeth and gums in the actual space. The complete digital 3D model of teeth is built by digital gingival retraction, which can export 3D files.

BACKGROUND OF INVENTION

The global market of fixed false tooth grows continuously. In terms of the fabrication of fixed false tooth, the patient's tooth must be prepared before gingival retraction to expose the ground tooth hidden in the gum before impression. However in the impression process, the accuracy, dimensional stability and operating variable can influence the precision of the finished false tooth directly.

The dental impression methods include traditional impression and digital impression. In terms of traditional impression, the first step is gingival retraction to expose the ground tooth hidden in the gum, so as to avoid impressing the tooth and gum at the same time that leads to unprepared margin impression of tooth, and then the false tooth margin made according to this impression will be imprecise. The gingival retraction modes include mechanical and mechanical-chemical modes. The former one simply pushes away the gum laterally with mechanical force. The latter one uses special cotton thread and chemical gingival retraction solution. There are two main classes of chemical gingival retraction solution, which are vasoconstrictor and astringent, both of them are effective on hemostasis, so they are favorable for impression taking. The dentists mostly use the gingival retraction method of mechanical-chemical gingival retraction cords for gingival retraction. The gingival cord is pressed in the gingival trough, the gum is pushed away horizontally with mechanical force, and the exudate and blood from the gingival trough are controlled by the chemical gingival retraction solution in the cord. This method shall press the gingival cord in the fine gingival trough with extruding force, so as to separate the tooth from the gum. The gingival cord is extracted during impression, thus the dental margin on the impression is very clear, and the dental impression technician can make the false tooth accurately according to this model. In the course of gingival retraction, the special gingival cotton thread for arresting bleeding shall be squeezed into the gingival trough, so the gingival retraction process not only takes time, but also discomforts the patient, and there are problems, such as unclear tooth shaping and gingival retraction in the treatment area, bleeding and intraoral moisture control in the treatment area, dimensional fit of impression tray, operation localization of impression tray, the blocking and discomfort of the patient's mouth resulted from the impression tray, insufficient impression material operating time, quality and contamination of impression material, mixing ratio of impression material, patient's nausea resulted from peculiar smell of impression material, deformation resulted from different flow paths and mixing ratios of gypsum, and the errors resulted from the manual finishing of gypsum pattern.

The most popular digital impression technique has been developed for three-dimensional appearance of tooth, which is more sanitary, convenient and faster than traditional impression technique. At present, many manufacturers have developed the digital impression technique. There are two main forms, one uses blue Light Emitting Diode (LED), this method needs a contrast medium or powder to obtain the tooth surface configuration. The other method uses laser technology for scanning, and the tooth surface is measured to acquire image. However, said two digital impression techniques cannot obtain the contour information of the tooth under the gum before gingival retraction. Therefore, to make the false tooth by using current digital impression technique for the patient, said gingival retraction method of gingival retraction cord shall be used for gingival retraction, so as to obtain the tooth contour hidden in the gum. In other words, the traditional impression or current digital impression requires said gingival retraction method of gingival retraction cord for gingival retraction, thus, the patient is likely to have gingival bleeding, and the patient is discomforted in the fabrication of false tooth, and the patient's periodontal ligament may tear.

SUMMARY OF INVENTION

In view of this, the present invention provides an optical tomography digital impression imaging system and method for use thereof, which relates to an imaging method for identifying two different media and the boundary, especially identifying the boundary between two different tissues in an organism, e.g. the boundary between tooth and gum. The present invention uses optical coherence tomography (OCT) technique to obtain the structural information of tooth surface and the boundary between tooth and gum under gum, and the refractive index of tissue is compensated to correct the authentic space thickness, and then the image of gum is removed (i.e. digital gingival retraction; optical gingival retraction), so as to build the complete digital 3D model containing the tooth inside and outside the gum.

The present invention provides an optical tomography digital impression imaging system, comprising an optical coherence tomography scanner and an information analysis and processing component. The optical coherence tomography scanner captures a plurality of optical tomography digital images. Each optical tomography digital image contains a plurality of tissue regions. The tissue regions include a tooth region and a gum region. A tomographic slice thickness of each tissue region in the optical tomography digital images is obtained, the tomographic slice thickness is an optical path. The information analysis and processing component is electrically connected to the optical coherence tomography scanner. The information analysis and processing component analyze the surface position of a target tissue region and a junction boundary between the target tissue region and adjacent tissue region, and then the optical path length (OPL) is obtained according to the longitudinal distance (light path direction) of boundary. A corrected tomographic slice thickness and a corrected junction boundary of the corresponding tissue region are obtained by correcting refractive indexes, a digital model of the target tissue region is built by the surface position, the corrected junction boundary and the corrected tomographic slice thickness of the tissue regions.

According to an embodiment of the present invention, there are an image storage and output unit and a 3D data storage unit, is electrically connected to the information analysis and processing component, to export an image and file of digital model.

According to an embodiment of the present invention, there is a probe, which is electrically connected to the optical coherence tomography scanner.

According to an embodiment of the present invention, the probe is a hand-held scanning probe in variable forms and sizes.

According to an embodiment of the present invention, the probe has a swinging galvanometer, is used to be aligned with a tooth region and a gum region of the patient in non-invasive direct scanning mode.

In addition, the present invention provides a digital impression imaging method, comprising the following steps: (1) obtain a plurality of optical tomography digital images, each optical tomography digital image contains a plurality of tissue regions, and obtain a tomographic slice thickness of each tissue region by piling up the optical tomography digital images; (2) analyze a surface position of a target tissue region and a junction boundary between the target tissue region and adjacent tissue regions; (3) obtain a refractive index of each tissue region by step (2); (4) obtain a corrected tomographic slice thickness and a corrected junction boundary of the corresponding tissue region by correcting the refractive indexes, revert a stack of the optical tomography digital images from OPL to an actual space thickness and an actual space height; and (5) build a digital model of the target tissue region by the surface position, the corrected junction boundary and the corrected tomographic slice thickness of the tissue regions.

According to an embodiment of the present invention, the corrected tomographic slice thickness is obtained by dividing the slice tomographic slice thickness by refractive index.

According to an embodiment of the present invention, the tissue regions include a tooth region and a gum region According to an embodiment of the present invention, the digital model includes a tooth surface structure model and a subgingival tooth structure model.

According to an embodiment of the present invention, the refractive index is calculated by one of the refractive index estimation method, boundary deformation approximation method, total reflection angle approximation method, reference location approximation method and medium signal intensity difference comparison method.

The novel techniques and methods of "compensation of refractive index of tissue", "optical path correction" and "authentic 3D digital model reconstruction for dental tissue region under gum and tooth contour outside gum" provided by the present invention are better than traditional gingival retraction technique, the patient's bleeding resulted from gingival retraction and the potential gingival laceration can be prevented. The tooth surface position is detected by non-invasive scanning mode, and the boundary is marked by algorithm, the scanning precision is enhanced, the tooth surface is free of reflecting agent, stable stereo scanning (3-Dimensional) can be implemented for the patient's tooth, so as to build precision tooth model and false tooth.

Description of symbols in the attached figures: 100—optical tomography digital impression imaging system; 10—optical coherence tomography scanner; 20—information analysis and processing component; 30—image storage and output unit; a—length; b—length; G—gum; $n_1$—refractive index; $n_2$—refractive index; T—tooth; $\lambda_1$—the first incident ray; $\lambda_{12}$—the second incident ray; $\lambda_2$—the third incident ray; $\Theta_c$—critical angle of total reflection; S101~S105—various steps.

DETAILED DESCRIPTION OF THE INVENTION

The method disclosed in the embodiment of the present invention can be used in image capture device or computer system or microprocessor system which can be connected to image capture device. The execution steps of the embodiment of the present invention can be written into a software program, the software program can be stored in any recording media which can be identified and read by the microprocessing unit, or in objects and devices containing said recording media. The form is not limited, said objects can be hard disk, floppy disk, compact disc, ZIP, magneto optic device (MO), IC chip, RAM or any objects containing said recording media which can be used by whoever familiar with this technique.

The computer system can contain display unit, processor, memory, input device and storage device. The input device is used for importing image, text and command data into the computer system. The storage device is hard disk, CD-ROM or remote database connected via Internet, for storing system programs, applications and user data, and storing the software program written in the embodiment of the present invention. The memory is used for storing data or executed programs temporarily. The processor is used for operation and processing data. The display unit is used for displaying the output data. When the computer system executes the method in the embodiment of the present invention, the corresponding program is loaded into the memory to execute the method in the embodiment of the present invention with the processor. Finally, the result is displayed on the display unit or stored in the storage device.

Figure 1:
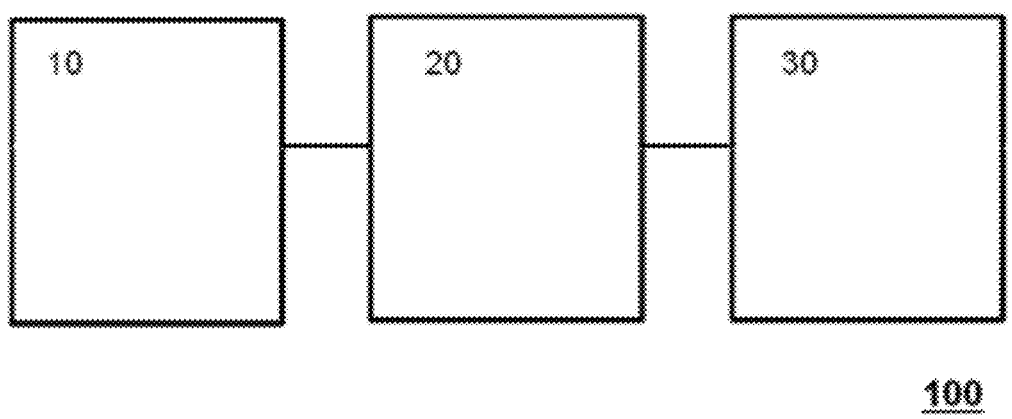
FIG. 1 is the schematic diagram of optical tomography digital impression imaging system of the present invention.
Figure 2:
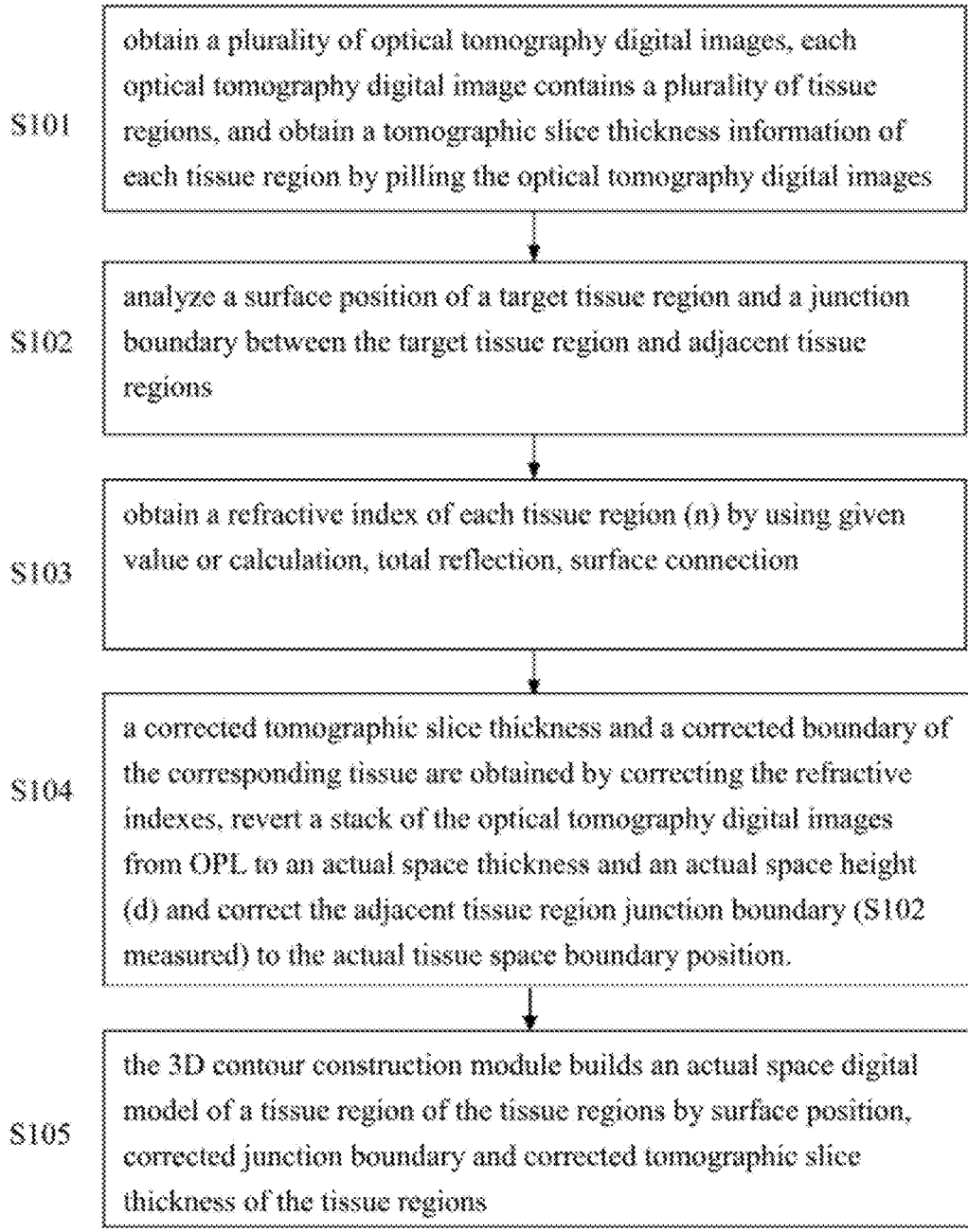
FIG. 2 is the flow chart of digital impression imaging method of the present invention.

An optical tomography digital impression imaging system 100 is provided by the present invention, comprising an optical coherence tomography scanner 10 and an information analysis and processing component 20 (as shown in FIG. 1). The optical coherence tomography scanner 10 captures a plurality of optical tomography digital images, each optical tomography digital image contains a plurality of tissue regions. The tissue regions include a tooth region and a gum region in the present invention, and a tomographic slice thickness of each tissue region in the optical tomography digital image is obtained. The tomographic slice thickness is an optical path (OPL) in the present invention. The information analysis and processing component 20 is electrically connected to the optical coherence tomography scanner 10. The information analysis and processing component 20 comprises OCT hardware control unit, OCT signal conversion processing unit and OCT information analysis processing unit (not shown). In an embodiment of the present invention, the OCT hardware control unit, OCT signal conversion processing unit and OCT information analysis processing unit are electrically connected to each other and held in information analysis and processing component 20. The OCT hardware control unit comprises a hardware scanning control module and an optical signal reading module (not shown). The OCT signal conversion processing unit comprises a signal conversion module, a noise processing module and an image distortion correction module (not shown). The OCT information analysis processing unit comprises a surface position judgment module, a tooth-gum boundary judgment module, a refractive index judgment module, an optical path correction module and a 3D contour construction module (not shown). For example, in an embodiment of the present invention, as shown in FIG. 2, the S103 is executed by refractive index judgment module, and the S104 is executed by optical path correction module.

Figure 3:
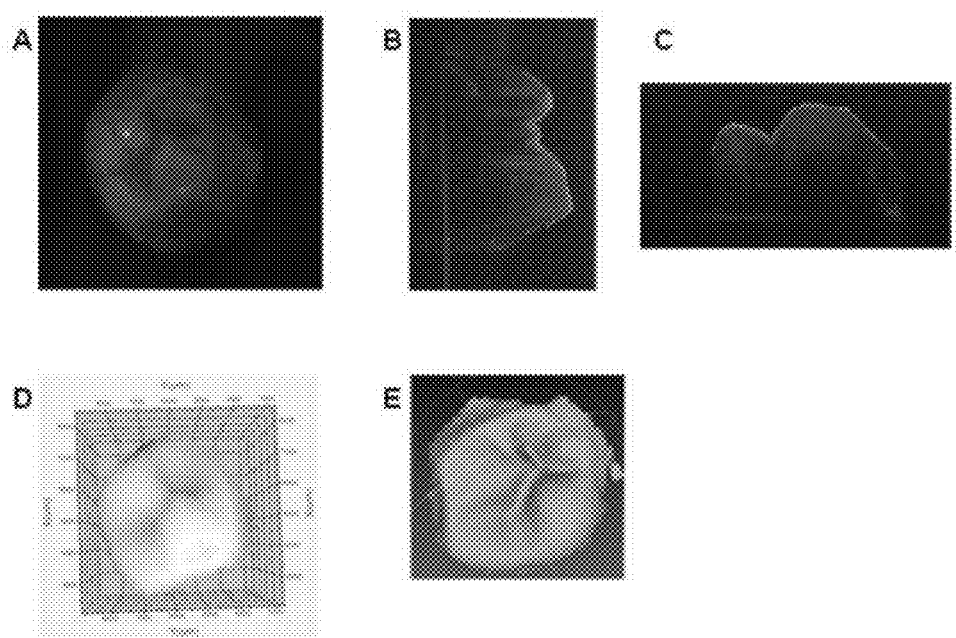
FIG. 3 is the tooth image captured by the optical tomography digital impression imaging system of the present invention.

Certainly, for convenient use and observation, the optical tomography digital impression imaging system 100 of the present invention comprises an image storage and output unit 30, is electrically connected to the information analysis and processing component 20, and an image of digital model is exported, e.g. a tooth surface structure model and an subgingival tooth structure model (see FIG. 1 and FIG. 3), and the image storage and output unit 30 comprises computer display module and 3D data storage module (not shown), and the 3D data storage module provides 3D stored data for other equipments to build the patient's false tooth.

In addition, a specific embodiment of the optical coherence tomography scanner 10 of the present invention is an infrared optical coherence tomography scanner. The optical tomography digital impression imaging system 100 of the present invention provides a digital impression imaging method, as shown in FIG. 2, comprising the following steps: (1) obtain a plurality of optical tomography digital images, each optical tomography digital image contains a plurality of tissue regions, and obtain a tomographic slice thickness information of each tissue region by pilling the optical tomography digital images (S101); (2) analyze a surface position of a target tissue region and a junction boundary between the target tissue region and adjacent tissue regions (S102); (3) obtain a refractive index of each tissue region (n) by using given value or calculation, total reflection, surface connection (S103); (4) obtain a corrected tomographic slice thickness and a corrected junction boundary of the corresponding tissue region by correcting the refractive indexes, revert a stack of the optical tomography digital images from OPL to an actual space thickness and an actual space height (d), and correct the junction boundary to surface position not judged by optical path correction S102 to the actual gum/tooth position (S104) as the actual position of tooth boundary in the gum for subsequent optical gingival retraction; and (5) build a digital model of the target tissue region by surface position, the corrected junction boundary and the corrected tomographic slice thickness of the tissue regions (S105), so as to provide the authentic 3D structure digital model of tissue region for the user. Which is to say, the present invention can implement the step of judging a surface position of a tissue region of the tissue regions and a junction boundary of tissue region and its adjacent tissue region (S102) by the surface position judgment module and tooth-gum boundary judgment module; implement the step of obtaining a refractive index of each tissue region (n) by using given value or calculation, total reflection and surface connection (S103) by refractive index judgment module; implement the step of using the refractive index corrections to obtain a corrected tomographic slice thickness and a corrected junction boundary of the corresponding tissue region, reverting the OPL to the actual space thickness (d) and correcting the junction boundary to surface position not judged by optical path correction S102 to the actual gum/tooth position (S104) by optical path correction module; and the step the 3D contour construction module builds an actual space digital model of a tissue region of the tissue regions by surface position, corrected junction boundary and corrected tomographic slice thickness of the tissue regions (S105).

The optical tomography digital impression imaging system provided by the present invention uses OCT technique, when a light source of optical tomography digital impression imaging system enters a tissue, said tissue in an embodiment of the present invention particularly refers to an organism tissue, the organism tissue feedback signal and reference signal implement interference, the information of tomographic slice thickness is obtained by interference. FIG. 3A shows an embodiment of using the optical tomography digital impression imaging system of the present invention to capture the top view of the tooth region of organism tissue. FIG. 3B shows the Y-axis slice of said tooth region. FIG. 3C shows the X-axis slice of said tooth region. FIG. 3D and FIG. 3E show the digital 3D diagram of tooth obtained by using the optical tomography digital impression imaging system of the present invention to scan the tooth region surface. The signal of tomographic slice thickness the present invention can obtain is the surface information of the first contact surface in the brilliant white line images in FIG. 3B and FIG. 3C.

Therefore, the tomographic slice thickness of organism tissue measured by OCT technique of the present invention is an optical path length (OPL). As the light travels in the organism tissue, the feedback signal is OPL, the optical path is affected by the refractive index (n). Therefore, the relation between the OPL and the corrected tomographic slice thickness of organism tissue is expressed as follows.

$$OPL = n \times d;$$

Namely, the authentic tomographic slice thickness correction relation of organism tissue is:

$$d = OPL/n$$

Where OPL is the optical path length, n is the refractive index, d is the corrected actual tomographic slice thickness of organism tissue. The present invention uses refractive index (n) as corrected parameter, the tomographic slice thickness of organism tissue measured by optical coherence tomography scanner 10 (OPL in the present invention) is converted by said effect relation into the corrected actual tomographic slice thickness of organism tissue (d). In other words, the corrected actual tomographic slice thickness of organism tissue (d) is obtained by dividing the OPL by refractive index in the present invention. In addition, the corrected tomographic slice thickness (d) refers to the actual tomographic slice thickness of tooth region in an embodiment of the present invention, or to the actual tomographic slice thickness of false tooth mold. However, the OCT technique only measures the OPL information of organism tissue, and the information for making false tooth mold is the actual tomographic slice thickness of tooth region (d), so the OPL deformation shall be corrected. In the tooth region or gum region of organism tissue, the OPL can be measured by optical tomography technique, but the actual tomographic slice thickness (d) and refractive index (n) are unknown, for the organism tissue, especially human tissue, the target tissue region to be measured cannot be excised to get the d value and n value. Therefore, to obtain the actual tomographic slice thickness of tissue region by using OCT technique, the refractive index (n) shall be obtained by using the system and its method of application disclosed in the present invention to correct the OPL, this is the refractive index compensation, i.e. OPL correction.

The present invention obtains the refractive index (n) of each tissue region, the refractive index (n) of tooth region and gum region is obtained by the information analysis and processing component 20. Please see S103 of FIG. 2, the refractive index of each tissue is obtained by refractive index judgment module in an embodiment of the present invention, and the refractive index (n) can be obtained by using one of the following methods: (1) refractive index estimation method: estimate an initial refractive index (this initial refractive index is applicable to different people with slightly different refractive indexes, and the information of this initial refractive index can be derived from database, in vitro measurement result and literature data), (2) boundary deformation approximation method: estimate the refractive index by boundary deformation (applicable to tooth projection, e.g. juncture between tooth and gum), (3) total reflection angle approximation method: the angle of total reflection of total reflection phenomenon is estimated as initial refractive index, when the total reflection is used, the OCT light source is reflected completely, so that the specific point generates the slice signal of junction transition; when the OCT is used in the angle of total reflection, the slice signal limit point and the angle of junction tangent are used as parameters, the result is the initial refractive index, (4) reference location approximation method: the other body parts of the same patient, especially the symmetric parts, are used as reference, the refractive index is measured as initial value (compared with the measured tomographic slice thickness, for example, the left molar region of the same patient is replaced by the number of right molar teeth), (5) tissue signal intensity difference comparison method: the tooth-gum junction is judged according to the difference between the tooth region tissue signal intensity and gingival tissue region signal intensity and compared with the fitting result.

Figure 4:
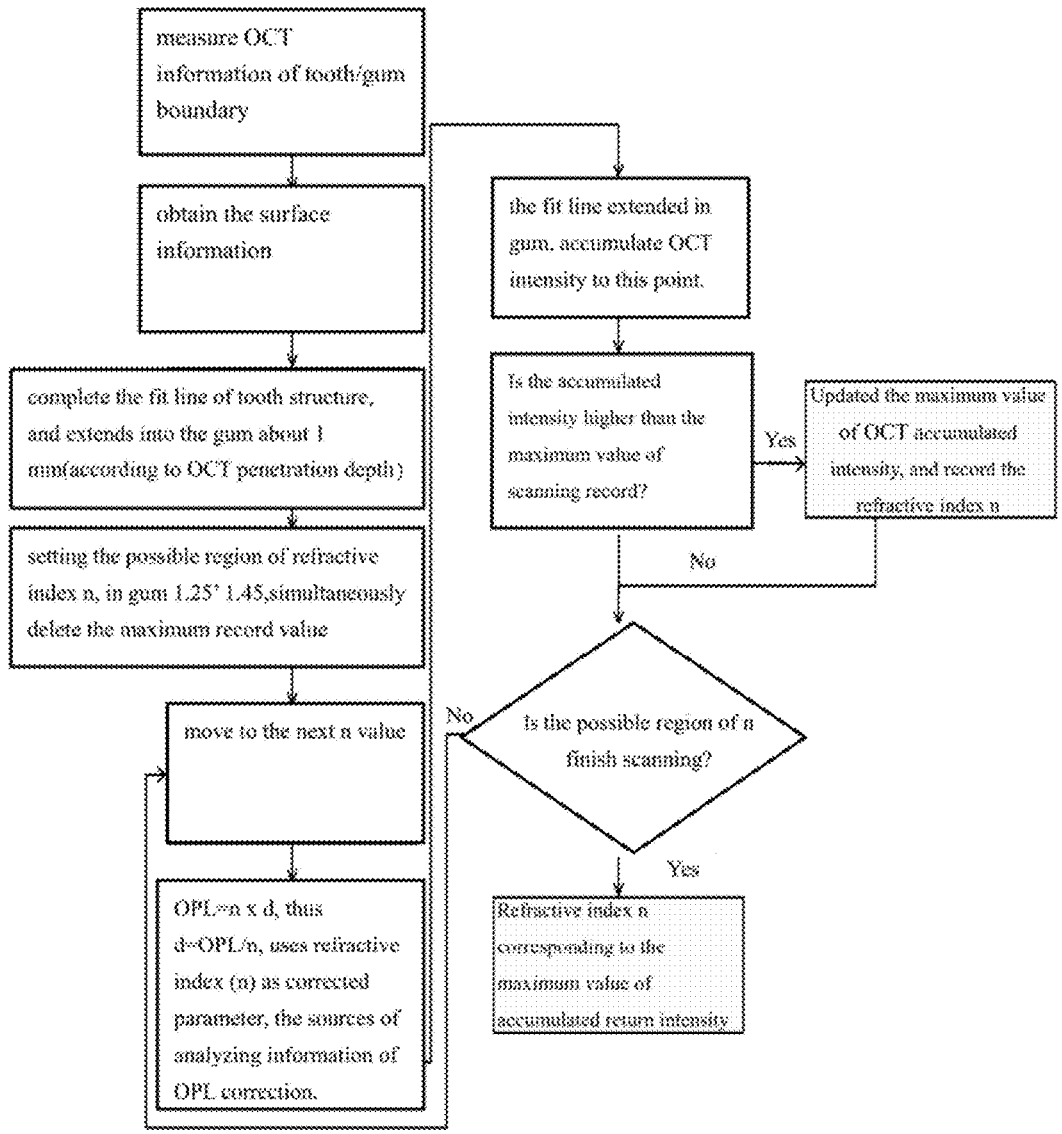
FIG. 4 is the flowchart of refractive index compensation of the present invention obtained by boundary deformation approximation method.

In said "boundary deformation approximation method", the process of obtaining refractive index (n) is shown in FIG. 4, which is the original OCT image of strong OCT reflected signal generated by the optical tomography digital impression imaging system 100 of the present invention at the boundary between two different tissues, e.g. the boundary between tooth region and gum region in an embodiment of the present invention. There is OPL deformation in the gum (FIG. 5A), when the exposed tooth extends into the gum, as the information measured by OCT is OPL, there will be an obvious turn when there is medium like gum. The tooth is continuous surface, an optimal refractive index n can be obtained by extending the exposed tooth into the gum for correction. Furthermore, the acquisition of the refractive index of the boundary deformation approximation method is described below: (a) obtain the image of tissue surface, (b) obtain a fit line, (c) when the fit line matches the tooth-gum junction boundary, the fit line coincides with the tooth-gum junction boundary, there will be a maximum intensity accumulated value (FIG. 5B), the fit line is accumulated for judgment. In addition, this boundary deformation approximation method uses the refractive index n to obtain the curve matching the estimated value. The image after OPL correction is shown in FIG. 5C. The fit line matches the tooth-gum junction boundary. In addition, FIG. 5D shows the result of correction by said method. The fit line in FIG. 5C is removed, and the fit line matches the tooth-gum junction boundary.

Figure 6:
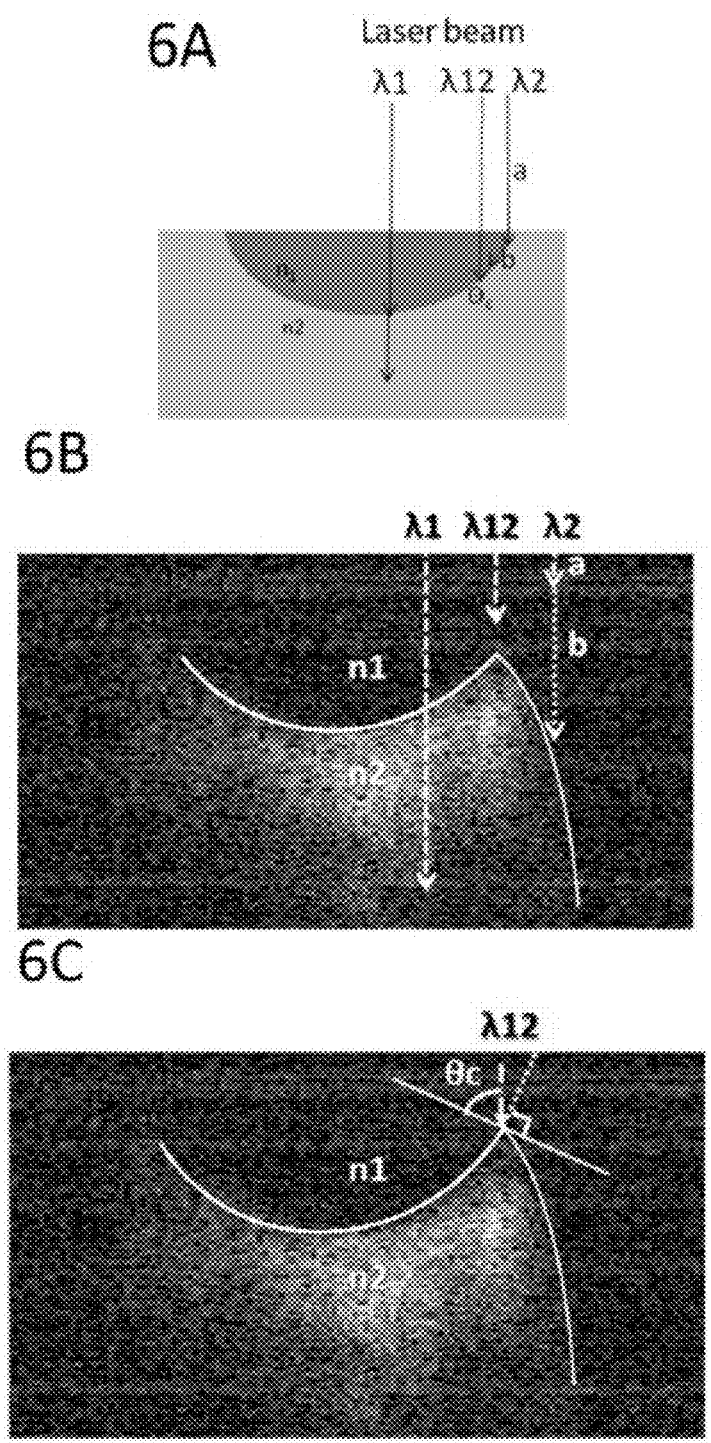
FIG. 6 shows an embodiment of refractive index compensation of the present invention by total reflection angle approximation method.

Referring to FIG. 6, in an embodiment of "total reflection angle approximation method", the refractive index is obtained by using total reflection phenomenon as initial refractive index, the schematic is shown in FIG. 6A. The light of high refractive index (n1) tissue shoots into low refractive index (n2) tissue, the total reflection behavior occurs when the incident angle is larger than the critical angle ($\Theta c$), this is applicable to where the refractive index of analyte can be measured directly without extending into another tissue (e.g. gum) junction boundary. At this point, the angle is $\Theta c=\mathrm{Sin}-1(n2/n1)$. Therefore, the method to obtain lower refractive index n2 is $n2=n1 \times \mathrm{Sin}\,\Theta c$. In terms of the actual implementation of an embodiment of the present invention, the tissue greater than the refractive index n2 of tissue to be measured is obtained as n1, and n1 is affixed to the tissue to be measured without gaps. The OCT is used to measure the n1, the OCT light beam is reflected completely in total reflection, the limit point position of slice information is generated, the included angle between the light at the limit point and the junction tangent is analyzed to obtain $\Theta c$. The n1 is given, so n2 is obtained, and n2 is fed back to correct the information of tomographic slice thickness measured by OCT. At this point, n1 is the given refractive index (the attached material is quartz), $\Theta c$ can obtain the position of initial total reflection at the tomography signal turn, so the refractive index of n2 (e.g. gum) can be calculated. In an embodiment, n1 is quartz (n~1.55); n2 is gum (n~1.4), meeting the total reflection characteristics. As shown in FIG. 6, a curved surface (quartz surface) clings to the gum, the interface is free of air, which is to say, the quartz with arc surface is used as the material with given refractive index (n1) to measure the gum with unknown refractive index (n2). In addition, in FIG. 6, $\lambda 1$ is the first incident ray, where the total reflection has not occurred; $\lambda 12$ is the second incident ray, where the total reflection begin to occur; $\lambda 2$ is the third incident ray, where the total reflection occurs. The curved material is scanned by OCT, on the n1 and n2 sections, there will be the difference between the first incident ray ($\lambda 1$) without total reflection and the third incident ray ($\lambda 2$) with total reflection of OCT light beam and the second incident ray ($\lambda 12$) with initial total reflection. The first incident ray has not exceeded $\Theta c$, so the OCT information has the tomographic slice thickness information of n2 (gum) and the contour is the curved surface of n1 medium. The third incident ray has exceeded $\Theta c$, leading to total reflection. Therefore, the actual length of light beam is a+b, the actual OPL is lengthened, the measured interface location is deep. The second incident ray ($\lambda 12$) is the position where the total reflection begins to occur, the OCT slice is taken as the interface turn, the position the total reflection begins to occur is the position where the $\Theta c$ occurrence point and angle are obtained. In the OCT scanning graph, the Θc occurrence point (λ12) and angle can be calculated by the following equation:

$$n2 = n1 \times \sin \Theta_c$$

The n2 is calculated and fed back as the refractive index of corrected OPL.

Moreover, FIG. 6B shows the embodiment of "total reflection angle approximation method", FIG. 6A is the schematic diagram of light beam paths without and with total reflection, where λ1 represents no total reflection behavior; λ12 is the position the total reflection begins to occur, the OCT measures a turning change in the interface; λ2 is the total reflection OCT light beam, so the actual length of light beam is a+b in total reflection of OCT. FIG. 6B shows the OCT slice, the λ2 total reflection light beam path measured by OCT system is a+b, so the measured junction is deeper, and limit point λ12 is the critical point generating total reflection. FIG. 6C shows the acquisition of Θc on critical angle. The OCT slice image is used in the occurrence position of angle of total reflection, the critical angle of total reflection Θc can be obtained by using the normal line (white solid line) normal to the surface tangent (white dotted line), and incident beam λ12, and n2 is obtained from n2=n1×sin θc.

Figure 7:
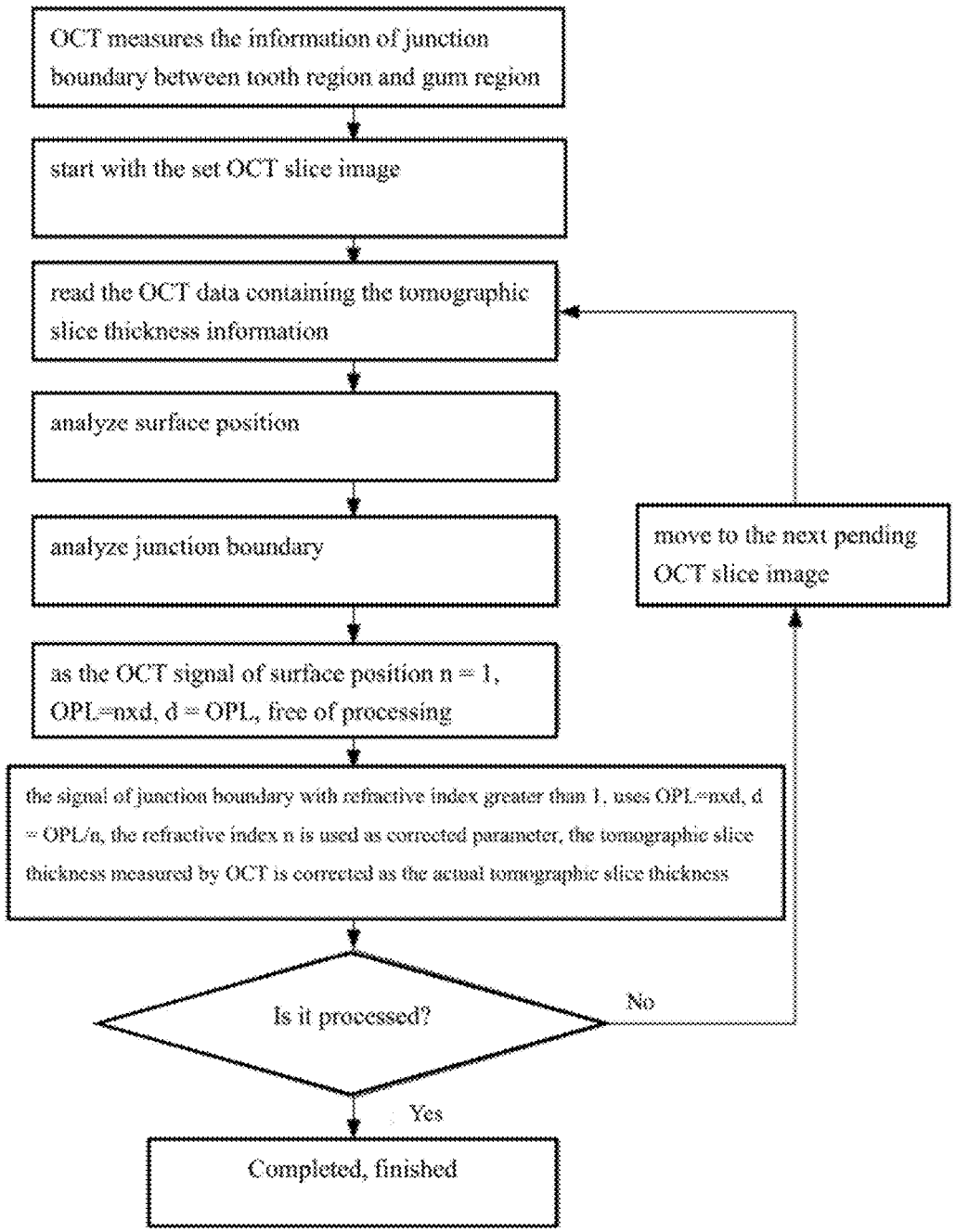
FIG. 7 is the flowchart of measuring tooth region and gum region by OPL correction of the present invention.

To sum up, the tooth region and gum region measured by OPL correction of the present invention are shown in FIG. 7. The original OCT tomographic slice thickness is compensated by the refractive index information to obtain the actual tomographic slice thickness of tissue region. The steps include (1) OCT measures the information of junction boundary between tooth region and gum region; (2) start with the set OCT slice image; (3) read the OCT data containing the tomographic slice thickness information; (4) analyze a surface position of a tissue region in the tooth region and gum region and a junction boundary between the tooth region and its adjacent gum region; (5) as the OCT signal of surface position n=1, in the actual tomographic slice thickness correction relation d=OPL/n, d=OPL, free of processing; (6) for the signal of junction boundary with refractive index greater than 1, in the actual tomographic slice thickness correction relation d=OPL/n, the refractive index n is used as corrected parameter, the tomographic slice thickness measured by OCT is corrected as the actual tomographic slice thickness of tissue region, e.g. tooth region or gum region. In addition, if the actual tomographic slice thickness has been obtained in this step, the OPL correction process is completed. In an embodiment of the present invention, the optical path correction module implements S104 in FIG. 2, a corrected tomographic slice thickness and a corrected boundary of the corresponding tissue are obtained by correcting the refractive indexes, revert a stack of the optical tomography digital images from OPL to an actual space thickness and an actual space height (d) and correct the adjacent tissue region junction boundary (S102 measured) to the actual tissue space boundary position. However, if the actual tomographic slice thickness has not been obtained in this step, proceed to the next OCT tomographic slice thickness image to be processed, and the OCT data containing tomographic slice thickness information are read again. The present invention can use said OPL correction to measure the actual tomographic slice thickness of tooth region and gum region, and to obtain a digital model of tissue region.

Figure 8:
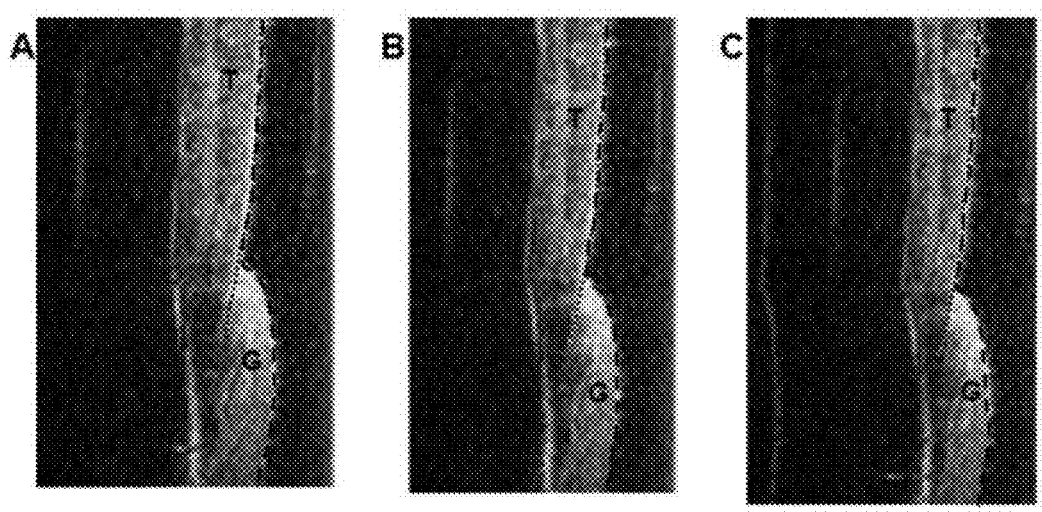
FIG. 8 is the first comparison diagram of images corrected by optical path difference of the present invention.

After the refractive index correction of information analysis and processing component 20, the fit line of tooth surface can be obtained (dotted line "....." in FIG. 8). In addition, the "-·-" and "----" in FIG. 8 represent the surface of tooth T and gum G. As shown in FIG. 8B, after the optical path difference is corrected appropriately, the dotted line of fit line coincides with the actual boundary between tooth T and gum G. If the optical path difference correction is insufficient, the junction boundary between tooth T and gum G is located below the dotted line of fit line in FIG. 8A. If the optical path difference is overcorrected, the junction boundary between tooth T and gum G is located above the dotted line of fit line in FIG. 8C.

Figure 5:
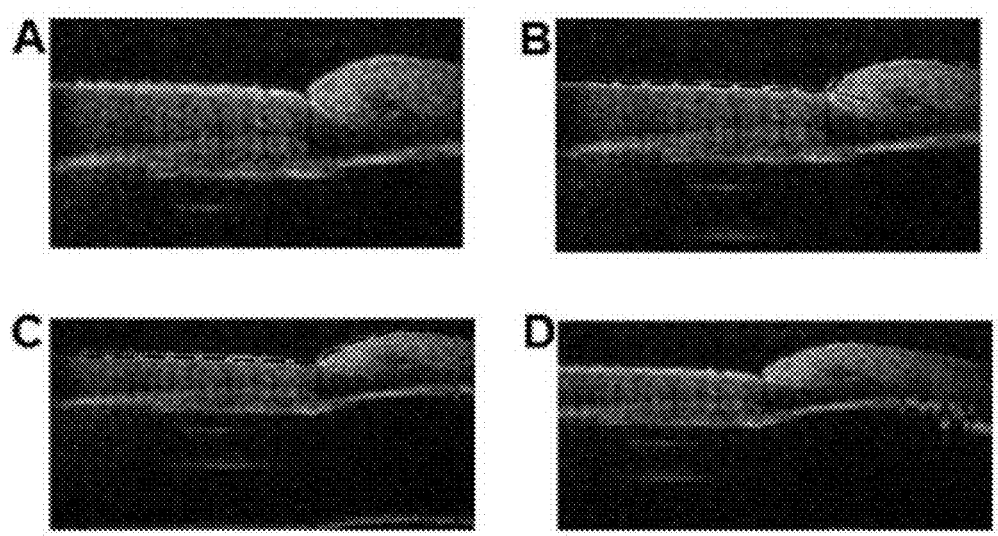
FIG. 5 shows the image of refractive index compensation of the present invention obtained by boundary deformation approximation method.
Figure 9:
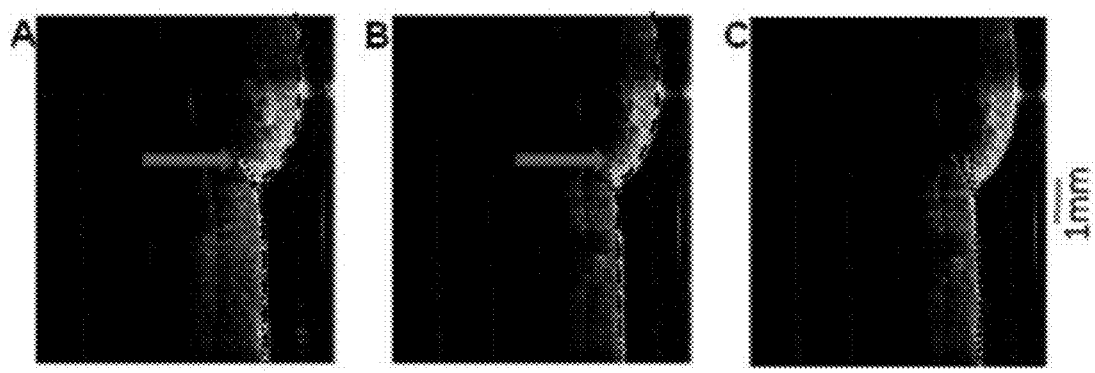
FIG. 9 is the second comparison diagram of images corrected by optical path difference of the present invention.

As stated above and as shown in FIG. 5 and FIG. 8, the optical tomography digital impression imaging system 100 of the present invention can identify the junction boundary between tooth region and gum region effectively, and can remove the image of one tissue region of two adjacent tissue regions by refractive index compensation and optical path difference correction, only leaving the image of the other tissue region to the user, i.e. the effectiveness of optical gingival retraction of gum image removal in an embodiment of the present invention. FIG. 9 shows the images before and after optical path difference correction of the present invention. FIG. 9A and FIG. 9B are the images before and after optical path difference correction of the present invention. The arrow indicates the junction boundary between tooth and gum. FIG. 9C shows the images of junction boundary between tooth and gum before and after optical path difference correction of the present invention. The junction boundaries before and after optical path difference correction are represented by two dotted lines. The gap between the tooth-gum junction boundaries before and after correction is 0.33 mm. Therefore, for making the patient's false tooth model, the present invention uses said refractive index compensation and optical path difference correction to implement the digital gingival retraction (optical gingival retraction) of the present invention. The optical coherence tomography scanner 10 of the present invention obtains a tomographic slice thickness of several tissue regions in each optical tomography digital image, analyzed and processed by the information analysis and processing component 20 with refractive index compensation and optical path difference correction functions to obtain a corrected tomographic slice thickness of the corresponding tissue region, so as to build a digital model corresponding to a tissue region. Furthermore, the present invention uses the image storage and output unit 30 to export an image of said digital model, and the present invention exports the image of digital gingival retraction, so as to build the complete digital 3D model for the patient's tooth. For the dentists, dental impression technicians and false tooth technicians, the present invention solves the long-term problems in previous techniques that the structural information of tooth-gum boundary under the gum is affected by optical path difference, so that the boundary between tooth and gum cannot be identified accurately, and the false tooth model can be made without the known techniques, e.g. gingival retraction cord. The patient's false tooth can be made by using the complete digital 3D model of tooth in the present invention, and the false tooth can match the tooth-gum boundary in the gum accurately.

Certainly, the present invention is not limited to this, the present invention is applicable to a tissue region I (e.g. tooth in embodiment of the present invention), its partial tissue region extends into the bottom of tissue region of a tissue region II (e.g. gum in embodiment of the present invention), so as to judge the junction boundary between tissue region I and tissue region II, the complete digital 3D model only exports one tissue region and eliminates the other tissue region.

Furthermore, the present invention is not limited to this, another embodiment has a probe (not shown), the probe is a hand-held scanning probe in variable forms and sizes. The probe has a swinging galvanometer (not shown), it can extract a tooth surface structure information and an subgingival tooth structure information by non-invasive direct scanning according to different patients' oral conditions.

The preferred embodiment of the present invention is described above, not limiting the features of this invention. Any technical means related to the present invention are in the scope of this case. The technical personnel of this field can make improvements according to said description, these changes are still in the spirit of the present invention and the scope of protection defined below.

What is claimed is:

1. An optical tomography digital impression imaging system, comprising:
    an optical coherence tomography scanner, the optical coherence tomography scanner captures a plurality of optical tomography digital images, each optical tomography digital image contains a plurality of tissue regions, and a tomographic slice thickness of each tissue region in the optical tomography digital images is obtained; and
    an information analysis and processing component, is electrically connected to the optical coherence tomography scanner,
    wherein information analysis and processing component comprises an OCT hardware control unit, an OCT signal conversion processing unit and an OCT information analysis processing unit, and
    wherein the OCT information analysis processing unit comprises a surface position judgment module, a tooth-gum boundary judgment module, a refractive index judgment module, an optical path correction module and a 3D contour construction module.

2. The optical tomography digital impression imaging system of claim 1, wherein the OCT hardware control unit comprises a hardware scanning control module and an optical signal reading module.

3. The optical tomography digital impression imaging system of claim 1, wherein the OCT signal conversion processing unit comprises a signal conversion module, a noise processing module and an image distortion correction module.

4. The optical tomography digital impression imaging system of claim 1, further comprises an image storage and output unit, is electrically connected to the information analysis and processing component, and an image of digital model is exported.

5. The optical tomography digital impression imaging system of claim 1, further comprises a probe, wherein the probe is electrically connected to the optical coherence tomography scanner.

6. The optical tomography digital impression imaging system of claim 5, wherein the probe is a hand-held scanning probe in variable forms and sizes.

7. The optical tomography digital impression imaging system of claim 6, wherein the probe has a swinging galvanometer, is used to be aligned with a tooth region and a gum region of the patient in non-invasive direct scanning mode.

8. A digital impression imaging method, comprising the following steps:
    (1) obtain a plurality of optical tomography digital images, each optical tomography digital image contains a plurality of tissue regions, and obtain a tomographic slice thickness of each tissue region by piling up the optical tomography digital images;
    (2) analyze a surface position of a target tissue region and a junction boundary between the target tissue region and adjacent tissue regions;
    (3) obtain a refractive index of each tissue region by step (2);
    (4) obtain a corrected tomographic slice thickness and a corrected junction boundary of the corresponding tissue region by correcting the refractive indexes, revert a stack of the optical tomography digital images from OPL to an actual space thickness and an actual space height; and
    (5) build an actual space digital model of the target tissue region by the surface position, the corrected junction boundary and the corrected tomographic slice thickness of the tissue regions.

9. The method of claim 8, wherein the corrected tomographic slice thickness is obtained by dividing the tomographic slice thickness by refractive index.

10. The method of claim 8, wherein the tissue regions include a tooth region and a gum region.

11. The method of claim 10, wherein the digital model includes a tooth surface structure model and a subgingival tooth structure model.

12. The method of claim 8, wherein the refractive index is calculated by one of the refractive index estimation method, boundary deformation approximation method, total reflection angle approximation method, reference location approximation method and medium signal intensity difference comparison method.

* * * * *